United States Patent
Uma Shankar

(10) Patent No.: US 11,110,064 B2
(45) Date of Patent: Sep. 7, 2021

(54) GEL FORMULATION FOR TREATING DIABETIC FOOT ULCER INFECTIONS

(71) Applicant: SRM INSTITUTE OF SCIENCE AND TECHNOLOGY, Chennai (IN)

(72) Inventor: Marakanam Srinivasan Uma Shankar, Chennai (IN)

(73) Assignee: SRM INSTITUTE OF SCIENCE AND TECHNOLOGY, Chennai (IN)

( * ) Notice: Subject to any disclaimer, the term of this patent is extended or adjusted under 35 U.S.C. 154(b) by 0 days.

(21) Appl. No.: 16/221,540

(22) Filed: Dec. 16, 2018

(65) Prior Publication Data

US 2020/0188314 A1 Jun. 18, 2020

(51) Int. Cl.
| | |
|---|---|
| *A61K 9/50* | (2006.01) |
| *A61K 9/06* | (2006.01) |
| *A61P 17/02* | (2006.01) |
| *A61K 31/545* | (2006.01) |

(52) U.S. Cl.
CPC .............. *A61K 9/5078* (2013.01); *A61K 9/06* (2013.01); *A61K 9/501* (2013.01); *A61K 9/5015* (2013.01); *A61K 9/5026* (2013.01); *A61K 9/5089* (2013.01); *A61K 31/545* (2013.01); *A61P 17/02* (2018.01)

(58) Field of Classification Search
CPC ........ A61K 9/5078; A61K 9/06; A61K 9/501; A61K 9/5015; A61K 9/5026; A61K 9/5089; A61K 31/545; A61P 17/02
See application file for complete search history.

(56) References Cited

U.S. PATENT DOCUMENTS

| | | | |
|---|---|---|---|
| 7,651,694 B2* | 1/2010 | Lee .................. | A61P 43/00 424/420 |
| 2002/0054914 A1* | 5/2002 | Morcol ................ | A61K 39/39 424/491 |
| 2002/0068090 A1* | 6/2002 | Bell .................... | A61K 9/1611 424/491 |
| 2009/0041812 A1* | 2/2009 | Bell .................... | A61K 8/24 424/401 |
| 2016/0074520 A1* | 3/2016 | Trexler ............... | A61K 9/0051 424/9.1 |
| 2018/0028684 A1* | 2/2018 | Yeoman ............. | C08L 5/00 |

FOREIGN PATENT DOCUMENTS

WO WO-2009137074 A1 * 11/2009 ........... A61K 31/155

OTHER PUBLICATIONS

Udo-Chijioke. Aquasomes: Multilayered Nanoparticular Drug Delivery Systems. Ph.D. Thesis. Aston University, Birmingham, UK. Dec. 2016. 267 pages. (Year: 2016).*
Jain et al. Aquasomes: A Novel Drug Carrier. Journal of Applied Pharmaceutical Science 02(01); 2012:184-192. (Year: 2012).*

* cited by examiner

*Primary Examiner* — Robert A Wax
*Assistant Examiner* — Olga V. Tcherkasskaya
(74) *Attorney, Agent, or Firm* — The Roy Gross Law Firm, LLC; Roy Gross

(57) ABSTRACT

The present disclosure relates to a gel formulation for treating diabetic foot ulcer infections. The gel formulation comprises antibiotic loaded aquasomes, a gelling agent, a preservative, and a fluid medium. The gel formulation of the present disclosure can be used for treating diabetic foot ulcer infections in mammals.

16 Claims, 19 Drawing Sheets

GEL FORMULATION FOR TREATING DIABETIC FOOT ULCER INFECTIONS

FIELD

The present disclosure relates to a gel formulation for treating diabetic foot ulcer infections.

Definition

As used in the present disclosure, the following term is generally intended to have the meaning as set forth below, except to the extent that the context in which it is used indicates otherwise.

Aquasome: The term "Aquasome" refers to a delivery system that have three layered and self-assembled structure which consists of a nano crystalline core, carbohydrate coating and drug coating.

BACKGROUND

The background information herein below relates to the present disclosure but is not necessarily prior art.

Diabetic foot ulcer infections (DFUs) are frequent complication of diabetes that may lead to severe and persistent infection and, in extreme cases, to lower extremity amputation. Therapeutics usually involves the use of dressings, aiming to enhance the life quality of DFU patients, to alleviate pain, to deliver drugs and to reduce odors. The necessity to develop and improve the efficacy of wound dressings, particularly suitable for DFU treatment, has been a challenge for both researchers and clinicians.

Conventionally, the drugs used to treat DFUs have many drawbacks such as high systematic toxicity and low therapeutic efficacy often caused by poor drug bioavailability, frequently related to the stability, solubility, and nonspecificity of drugs. Recently, alternatives to conventional dressings, like hydrogels, films, and medicated wound dressings, have been developed using natural and synthetic polymers along with cross-linking loaded with antimicrobials/antibiotics. These compounds have been studied as a means to efficiently deliver to improve DFU treatment by decreasing the infection and inflammation in the chronic wound and to improve healing. However, these findings do not yet represent a practical option since application of these compounds did not provide positive improvement in patient care and quality of life.

Therefore, there is felt a need for a composition that mitigates the aforestated drawbacks.

OBJECTS

Some of the objects of the present disclosure, which at least one embodiment herein satisfies, are as follows:

It is an object of the present disclosure is to ameliorate one or more problems of the prior art or to at least provide a useful alternative.

An object of the present disclosure is to provide a gel formulation for treating diabetic foot ulcer infections.

Another object of the present disclosure is to provide a gel formulation that has improved therapeutic efficacy.

Still another object of the present disclosure is to provide a stable gel formulation.

Yet another object of the present disclosure is to provide a gel formulation with enhanced solubility.

Other objects and advantages of the present disclosure will be more apparent from the following description, which is not intended to limit the scope of the present disclosure.

SUMMARY OF THE INVENTION

In one aspect of the present disclosure, there is provided a gel formulation for treating diabetic foot ulcer infections. The formulation comprises antibiotic loaded aquasomes, a gelling agent, a preservative, and a fluid medium.

In accordance with an embodiment of the present disclosure, the formulation comprises antibiotic loaded aquasomes in an amount in the range of 15 wt % to 20 wt % of the total weight of the formulation, a gelling agent in an amount in the range of 70 wt % to 90 wt % of the total weight of the formulation, a preservative in an amount in the range of 0.05 wt % to 0.25 wt % of the total weight of the formulation, and a fluid medium in an amount in the range of 1 wt % to 4 wt % of the total weight of the formulation.

In one embodiment of the present disclosure, the formulation comprises antibiotic loaded aquasomes in an amount of 19.4 wt % of the total weight of the formulation, a gelling agent in an amount of 77.66 wt % of the total weight of the formulation, a preservative in an amount of 0.2 wt % of the total weight of the formulation, and a fluid medium in an amount of 2.74 wt % of the total weight of the formulation.

In accordance with an embodiment of the present disclosure, the antibiotic is cephalosporin.

In accordance with another embodiment of the present disclosure, the antibiotic is selected from cefprozil monohydrate and cefuroxime axetil. The gelling agent is selected from the group consisting of 2-propenoic acid homopolymer, acacia, pectin, methyl cellulose, ethyl cellulose, hydroxyl propyl methyl cellulose, and sodium alginate. The preservative is at least one selected from the group consisting of methyl paraben, propyl paraben, benzoic acid, sodium benzoate, and chlorocresol. The fluid medium is selected from the group consisting of water, ethanol, benzene, acetone, and phosphate buffer.

The particle size of the aquasomes is in the range of 80 nm to 120 nm, and zeta potential of the aquasomes is −29.8 mV.

The pH of the gel formulation is in the range of 6.0 to 7.0.

In another aspect of the present disclosure there is provided a process for preparing a gel formulation. The process comprises reaction of disodium hydrogen phosphate solution and calcium chloride solution under continuous stirring to obtain a first mixture comprising precipitated calcium phosphate. The precipitated calcium phosphate is separated from the first mixture and washing the precipitated calcium phosphate with water to obtain a calcium phosphate. The calcium phosphate is suspended in water and filtered to obtain a filtered calcium phosphate. The filtered calcium phosphate is lyophilized to obtain a core of calcium phosphate. The core of calcium phosphate and polyhydroxy oligomer are admixed to obtain a second mixture. The second mixture is sonicated for a time period in the range of 10 minutes to 20 minutes to obtain a suspension and then the suspension is settled at a temperature in the range of 2° C. to 8° C. for a time period in the range of 360 minutes to 600 minutes. The settled suspension is lyophilized to obtain a polyhydroxy oligomer coated calcium phosphate. Antibiotic and the polyhydroxy oligomer coated calcium phosphate are mixed under stirring for a time period in the range of 80 minutes to 100 minutes to obtain a third mixture. The so obtained third mixture is settled at a temperature in the range of 2° C. to 8° C. for a time period in the range of 360 minutes to 600 minutes. The settled third mixture is lyophilized to obtain antibiotic loaded aquasomes. The so obtained aquasomes are blended with a gelling agent, a preservative, and a fluid medium to obtain the gel formulation.

In yet another aspect of the present disclosure there is provided a method for the treatment of diabetic foot ulcer infections in mammals, comprising topical application of an effective amount of the gel formulation.

BRIEF DESCRIPTION OF THE DRAWINGS

The present disclosure will now be described with the help of the accompanying drawing, in which.

DETAILED DESCRIPTION OF THE INVENTION

Figure 1:
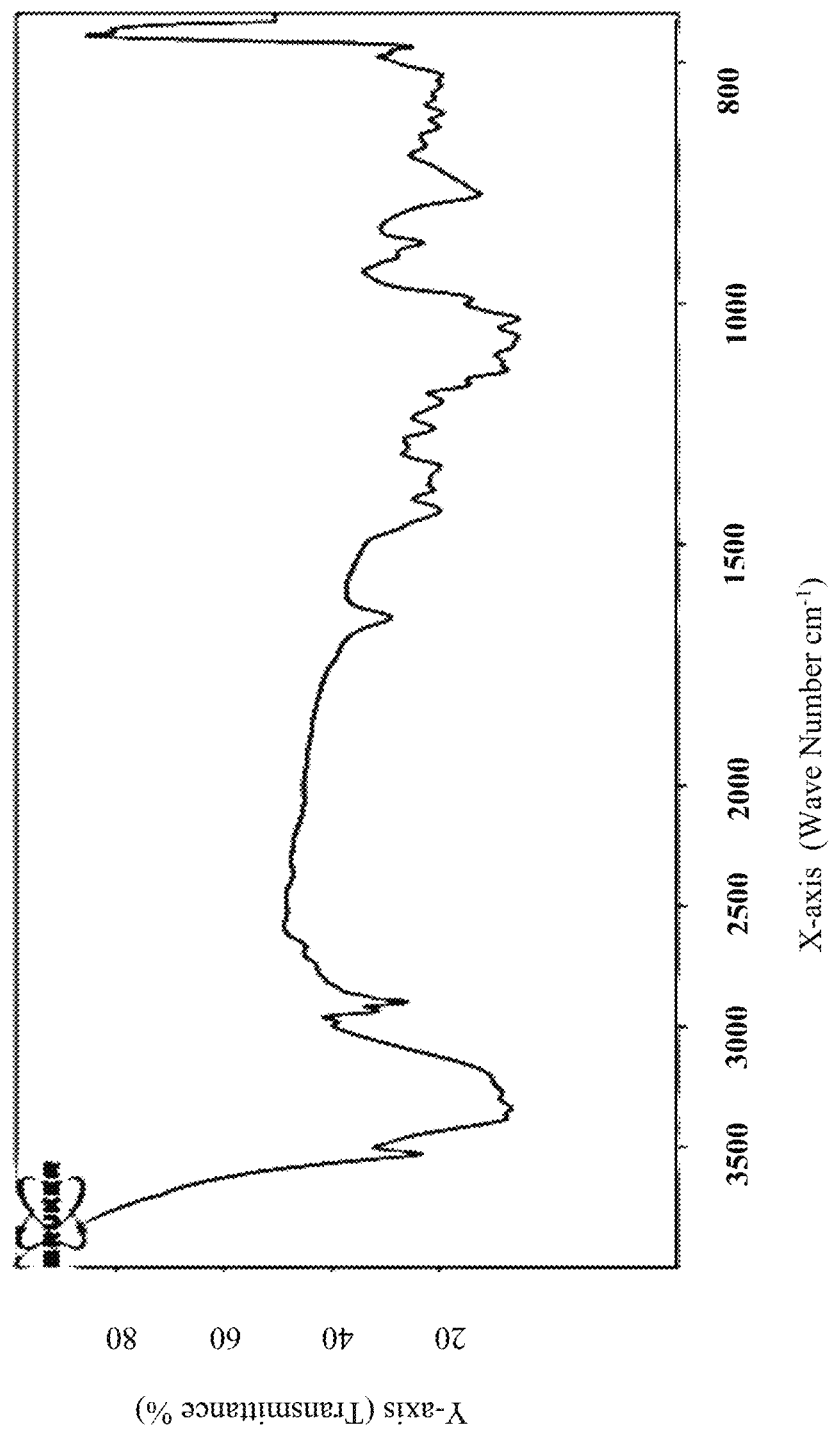
FIG. 1 depicts an FT-IR spectroscopy for calcium phosphate core, wherein 'X-axis' denotes wavenumber and 'Y-axis' denotes Transmittance (%).

Embodiments, of the present disclosure, will now be described with reference to the accompanying drawing.

Embodiments are provided so as to thoroughly and fully convey the scope of the present disclosure to the person skilled in the art. Numerous details, are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise. The terms "comprises," "comprising," "including," and "having," are open ended transitional phrases and therefore specify the presence of stated features, integers, steps, operations, elements, modules, units and/or components, but do not forbid the presence or addition of one or more other features, integers, steps, operations, elements, components, and/or groups thereof. The particular order of steps disclosed in the method and process of the present disclosure is not to be construed as necessarily requiring their performance as described or illustrated. It is also to be understood that additional or alternative steps may be employed.

As used herein, the term "and/or" includes any and all combinations of one or more of the associated listed elements.

The terms first, second, third, etc., should not be construed to limit the scope of the present disclosure as the aforementioned terms may be only used to distinguish one element, component, region, layer or section from another component, region, layer or section. Terms such as first, second, third etc., when used herein do not imply a specific sequence or order unless clearly suggested by the present disclosure.

Diabetic foot ulcer infections (DFUs) are frequent complication of diabetes. The treatment of DFUs involves the use of dressings, aiming to enhance the life quality of DFU patients, to alleviate pain, to deliver drugs and to reduce odors. The necessity to develop and improve the efficacy of wound dressings, particularly suitable for DFU treatment, has been a challenge for both researchers and clinicians. Also, the conventional drugs used for treating DFUs have many drawbacks such as high systematic toxicity and low therapeutic efficacy often caused by poor drug bioavailability, frequently related to the stability, solubility, and non-specificity of drugs.

Therefore, the present disclosure envisages a composition that mitigates the aforestated drawbacks.

In an aspect of the present disclosure, a gel formulation for treating diabetic foot ulcer infections is provided. The formulation comprises antibiotic loaded aquasomes, a gelling agent, a preservative, and a fluid medium.

In accordance with an embodiment of the present disclosure, the formulation comprises antibiotic loaded aquasomes in an amount in the range of 15 wt % to 20 wt % of the total weight of the formulation, a gelling agent in an amount in the range of 70 wt % to 90 wt % of the total weight of the formulation, a preservative in an amount in the range of 0.05 wt % to 0.25 wt % of the total weight of the formulation, and a fluid medium in an amount in the range of 1 wt % to 4 wt % of the total weight of the formulation.

In one embodiment of the present disclosure, the formulation comprises antibiotic loaded aquasomes in an amount of 19.4 wt % of the total weight of the formulation, a gelling agent in an amount of 77.6 wt % of the total weight of the formulation, a preservative in an amount of 0.2 wt % of the total weight of the formulation, and a fluid medium in an amount of 2.74 wt % of the total weight of the formulation.

In accordance with an embodiment of the present disclosure, the antibiotic is cephalosporin.

In accordance with another embodiment of the present disclosure, the antibiotic can be selected from cefprozil monohydrate and cefuroxime axetil.

In one embodiment of the present disclosure, the antibiotic is cefprozil monohydrate.

The gelling agent can be selected from the group consisting of 2-propenoic acid homopolymer, acacia, pectin, methyl cellulose, ethyl cellulose, hydroxyl propyl methyl cellulose, and sodium alginate. In one embodiment of the present disclosure, the gelling agent is 2-propenoic acid homopolymer.

The preservative is at least one selected from the group consisting of methyl paraben, propyl paraben, benzoic acid, sodium benzoate, and chlorocresol.

The fluid medium is selected from the group consisting of water, ethanol, benzene, acetone, and phosphate buffer.

In accordance with an embodiment of the present disclosure, the particle size of the aquasomes can be in the range of 80 nm to 120 nm, and zeta potential of the aquasomes is −29.8 mV.

In accordance with an embodiment of the present disclosure, pH of the gel formulation is in the range of 6.0 to 7.0. In one embodiment of the present disclosure, pH of the gel formulation is 6.9.

In another aspect of the present disclosure, there is provided a process for preparing a gel formulation. The process comprises preparation of an antibiotic loaded aquasome, followed by blending with a gelling agent, a preservative, and water to obtain the gel formulation. The process is hereinafter described in detail.

I. Antibiotic loaded aquasomes are prepared using the following steps:

In a first step, disodium hydrogen phosphate solution and calcium chloride solution is reacted under continuous stirring to obtain a first mixture comprising precipitated calcium phosphate. In one embodiment, the molar ratio of the disodium hydrogen phosphate solution to the calcium chloride solution is 1:1.

In a second step, the precipitated calcium phosphate is separated from the first mixture and the separated calcium phosphate is washed with water to obtain calcium phosphate.

In a third step, the calcium phosphate is suspended in water and filtered to obtain filtered calcium phosphate. In an embodiment, the filtration in third step is carried out using 0.22 μm millipore filter.

In a fourth step, the filtered calcium phosphate is lyophilized to obtain a core of calcium phosphate. The particle size of the core of calcium phosphate can be in the range of 45 nm to 55 nm.

In a fifth step, the core of calcium phosphate and a polyhydroxy oligomer are admixed to obtain a second mixture, and then the second mixture is sonicated for a time period in the range of 10 minutes to 20 minutes to obtain a suspension. The suspension is settled at a temperature in the range of 2° C. to 8° C. for a time period in the range of 360 minutes to 600 minutes. The polyhydroxy oligomer is selected from the group consisting of lactose, trehalose, and cellobiose.

In accordance with an embodiment of the present disclosure, the weight ratio of the polyhydroxy oligomer to the core of calcium phosphate is 1:2.

In a sixth step, the settled suspension is lyophilized to obtain a polyhydroxy oligomer coated calcium phosphate.

In the seventh step, antibiotic and the polyhydroxy oligomer coated calcium phosphate are mixed under stirring for a time period in the range of 80 minutes to 100 minutes to obtain a third mixture. The third mixture is settled at a temperature in the range of 2° C. to 8° C. for a time period in the range of 360 minutes to 600 minutes. In an embodiment, the weight ratio of the antibiotic to the polyhydroxy oligomer coated calcium phosphate is 1:2.

In the eighth step, the settled third mixture is lyophilized to obtain antibiotic loaded aquasomes.

II. The so obtained aquasomes are blended with a gelling agent, a preservative, and a fluid medium to obtain the gel formulation.

In yet another aspect of the present disclosure there is provided a method for treatment of diabetic foot ulcer infections in mammals. The method comprises topical application of an effective amount of a gel formulation, wherein the formulation comprises antibiotic loaded aquasomes, a gelling agent, a preservative, and a fluid medium.

In accordance with an embodiment of the present disclosure, the effective amount of the formulation can be in the range of 2 mg to 20 mg.

Overall, the gel formulation of the present disclosure has improved stability, and solubility. Also, the gel formulation has enhanced bioavailability and therapeutic efficacy while treating diabetic foot ulcer infections.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

The present disclosure is further described in light of the following experiments which are set forth for illustration purpose only and not to be construed for limiting the scope of the disclosure. The following experiments can be scaled up to industrial/commercial scale and the results obtained can be extrapolated to industrial scale.

EXPERIMENTAL DETAIL

Experiment 1: Preparation of Antibiotic Loaded Aquasomes

A. Preparation of Calcium Phosphate Core by Precipitation Method 25 ml of disodium hydrogen phosphate solution (0.75M) and 25 ml of calcium chloride solution (0.25M) was reacted under continuous stirring for 2 hours on a magnetic stirrer to obtain a first mixture comprising precipitated calcium phosphate. The precipitated calcium phosphate was separated from the first mixture by means of filtration and washed the separated calcium phosphate 3 times with 100 ml of distilled water to obtain a calcium phosphate. The calcium phosphate was suspended in water and filtered using 0.22 μm millipore filter to obtain a filtered calcium phosphate. The filtered calcium phosphate lyophilized to obtain a core of calcium phosphate.

The core of calcium phosphate was characterized by using FT-IR spectroscopy, Zeta sizer, X-ray powder diffractograms (XRD), and Scanning electron microscopy (SEM).

FT-IR spectroscopy was used for structural analysis of inorganic core (Calcium phosphate core). The characteristic bands observed for PO³₄ of Calcium phosphate at 425.02, 526.76, 576.95, 661.89, and 987.79 (FIG. 1). Hence, FIG. 1 confirms the formation of calcium phosphate core.

Figure 2:
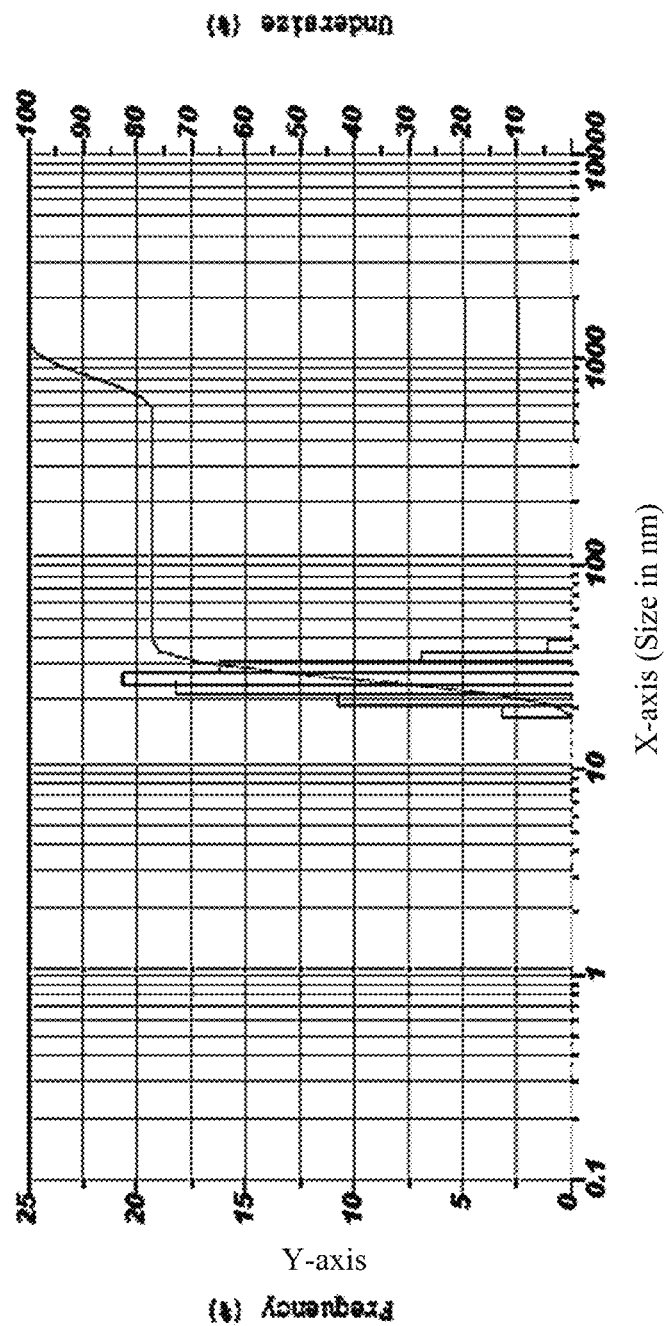
FIG. 2 depicts a graphical representation of particle size for calcium phosphate core.

The zeta potential of calcium phosphate core was determined by Zeta sizer using the principle of electrophoretic mobility under an electric field. Zeta potential was an indicator of surface charge, which determines particle stability in dispersion. The particle size of calcium phosphate core was given table 1. The mean particle size of the calcium phosphate core was found to be 46.5 nm (FIG. 2). Therefore, the mean particle size of the calcium phosphate core confirms the stability of the core of calcium phosphate.

TABLE 1

Particle size of calcium phosphate core

| Peak No. | S.P. Area Ratio | Mean | SD | Mode |
|---|---|---|---|---|
| 1 | 0.77 | 46.5 nm | 0.4 nm | 2.5 nm |
| 2 | 0.23 | 836.7 nm | 145.0 nm | 795.6 nm |
| 3 | — | — nm | — nm | — nm |
| Total | 1.00 | 46.5 nm | 357.2 nm | 2.5 nm |

Figure 3:
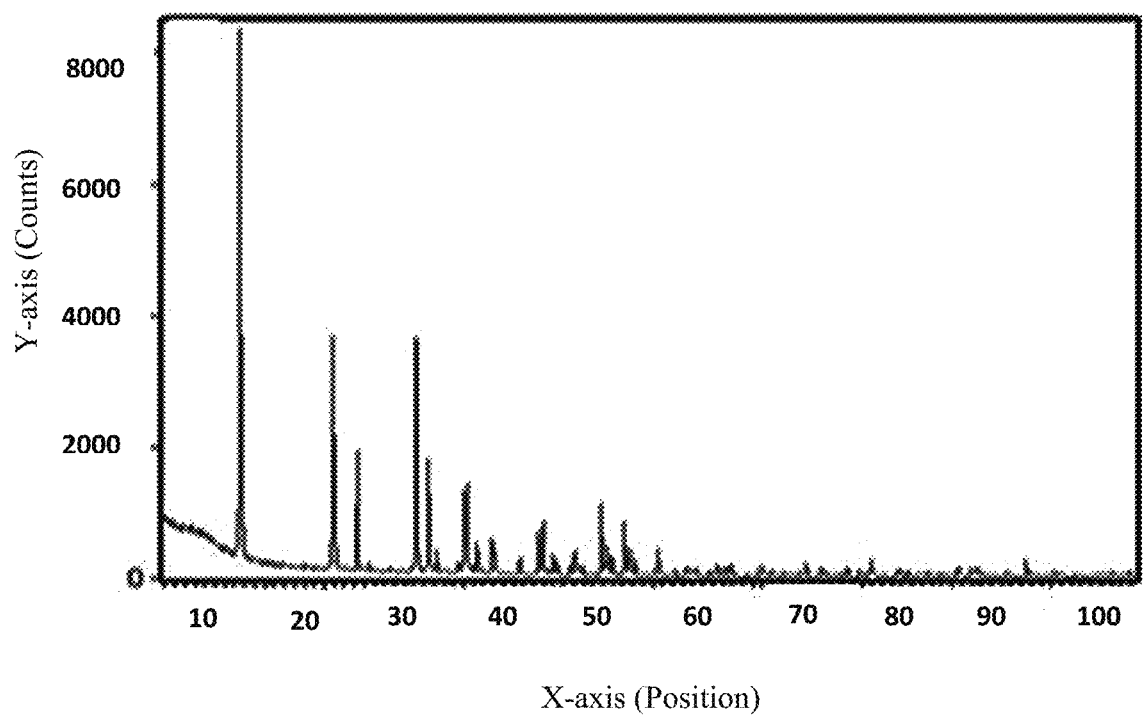
FIG. 3 depicts a X-ray powder diffractograms for calcium phosphate core, wherein 'X-axis' denotes Position [°2Theta] (Copper) and 'Y-axis' denotes counts.

The X-ray powder diffractograms peak clearly shows the crystalline nature of calcium phosphate core (FIG. 3).

The morphological analysis of calcium phosphate core was determined by SEM. Scanning electron microscopy of the calcium phosphate core shows elongated crystalline structures (FIG. 4).

Figure 4:
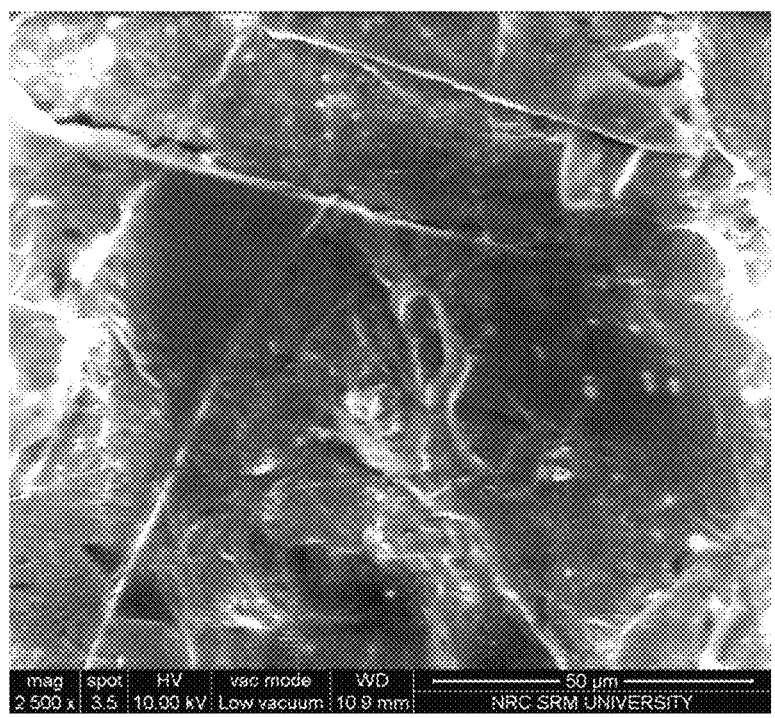
FIG. 4 depicts a Scanning electron microscopy of the calcium phosphate core.

From FIGS. 3 and 4, it is evident that the core of calcium phosphate was crystalline in nature and hence highly soluble.

B. Coating of Calcium Phosphate Core with Lactose

The core of calcium phosphate (200 mg) and lactose (100 ml) were admixed in a conical flask to obtain a second mixture. The second mixture was sonicated for 10 minutes to obtain a suspension and then the suspension was settled at 4° C. for 600 minutes. The settled suspension was lyophilized to obtain a lactose coated calcium phosphate. The formation of lactose coated calcium phosphate was confirmed using Anthrone reagent test.

Anthrone Reagent Test:

50 mg of lactose coated calcium phosphate core was accurately weighed and dissolved in 5 ml of distilled water. 2 ml of the above solution was added to 5.5 ml anthrone reagent and boiled (10 min, 100° C.). Appearance of green color confirmed the presence of lactose coating over calcium phosphate core.

The lactose coated core of calcium phosphate was characterized by using FT-IR spectroscopy, X-ray powder diffractograms (XRD), and Scanning electron microscopy (SEM).

Figure 5:
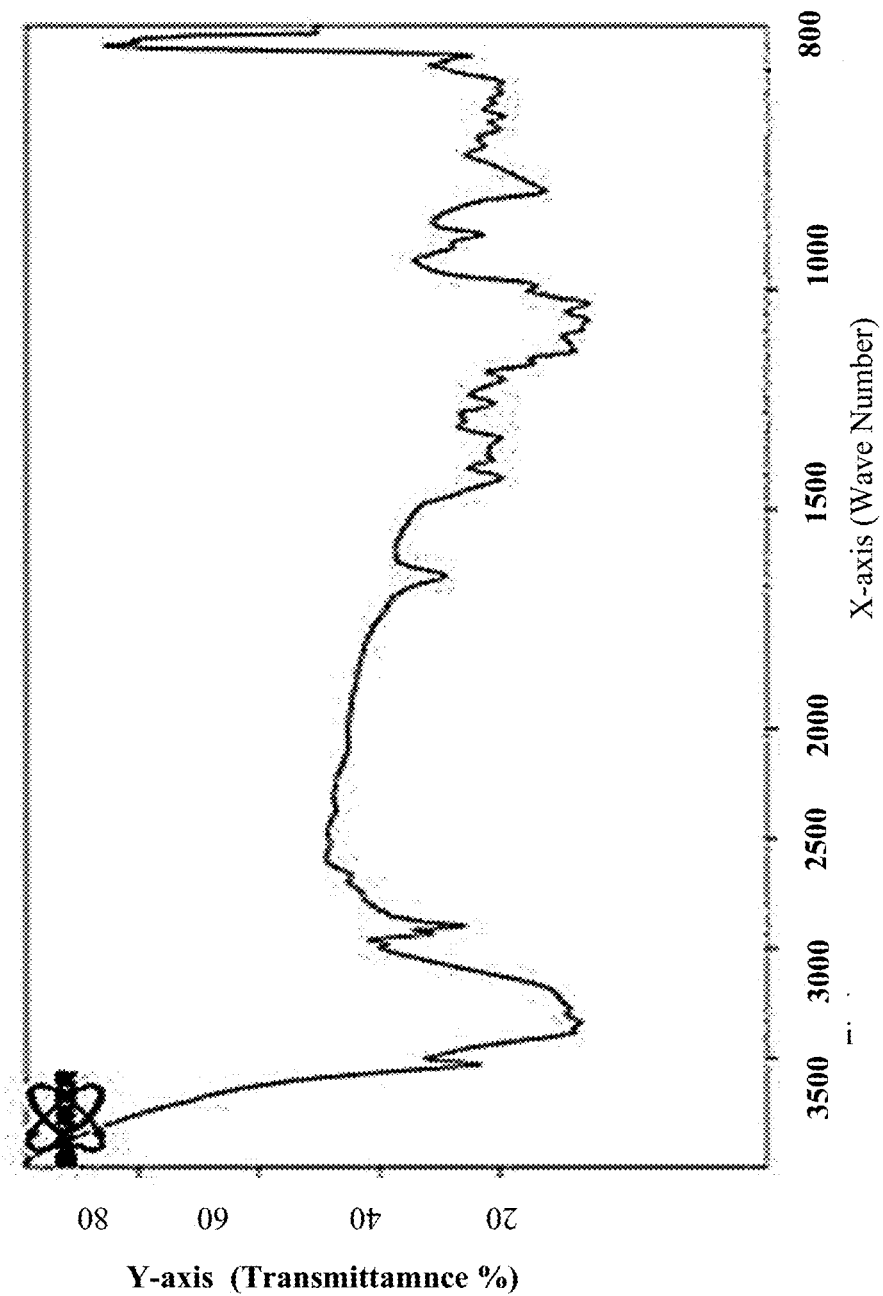
FIGS. 5-7 depict a FT-IR spectroscopy of calcium phosphate inorganic core coated with lactose having coating concentrations of a) 0.03 M, b) 0.06 M, and c) 0.09 M, respectively, wherein 'X-axis' denotes wavenumber and 'Y-axis' denotes Transmittance (%).
Figure 6:
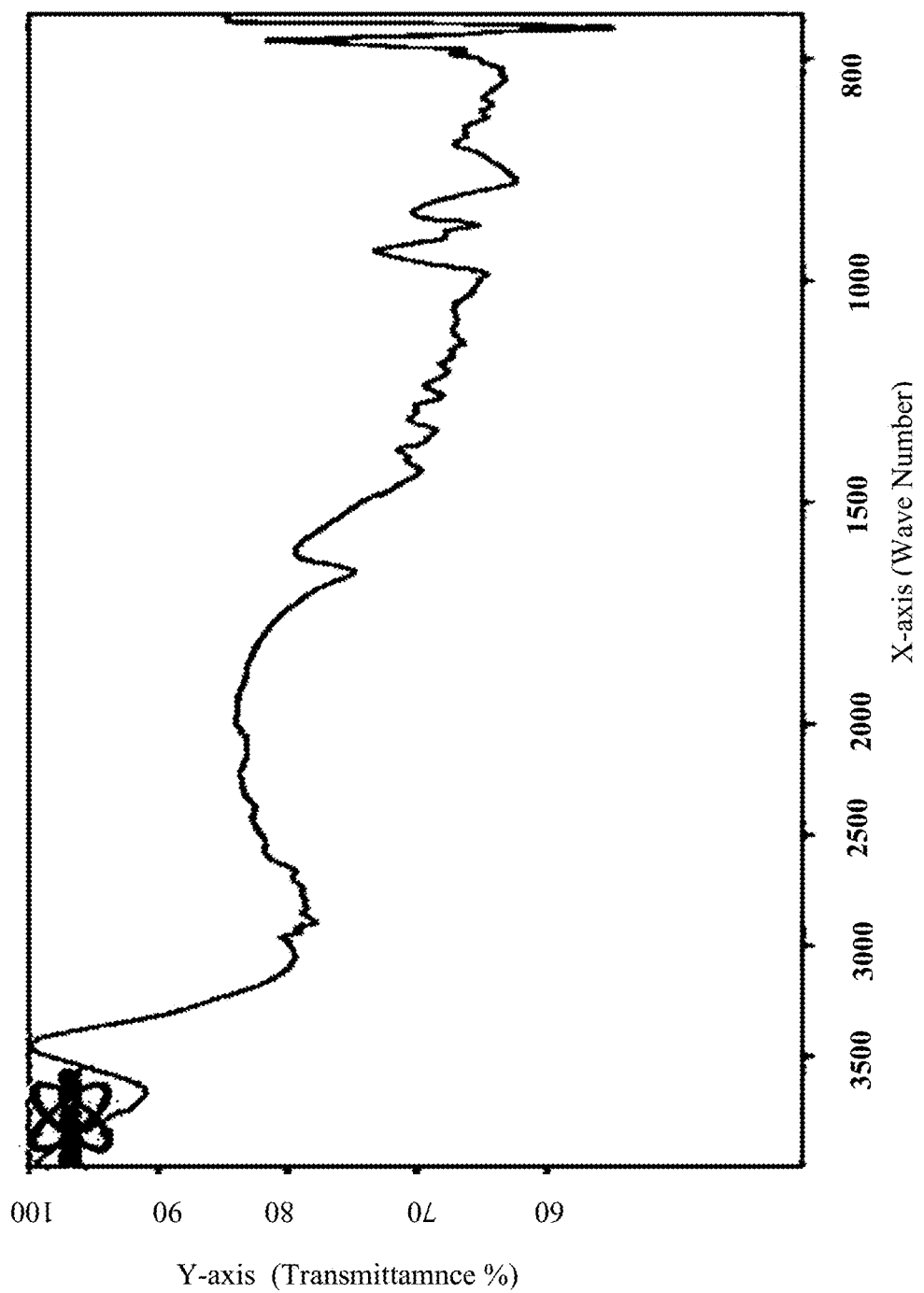
Figure 7:
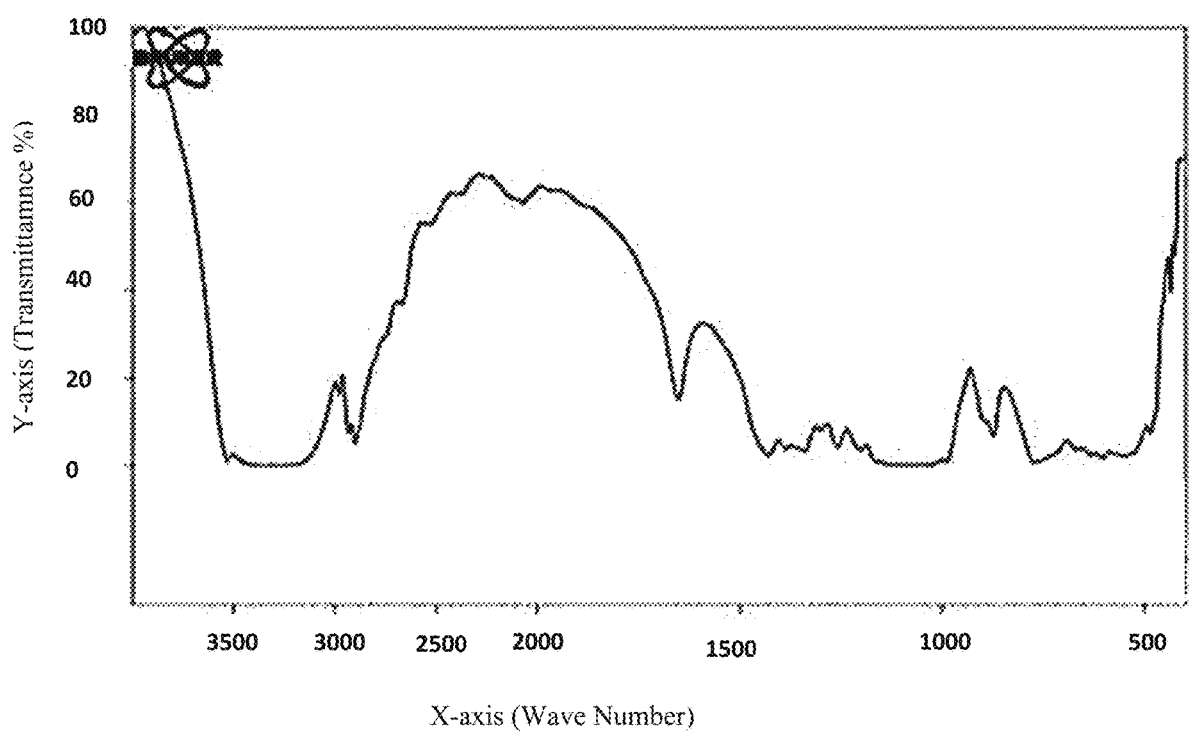

The FT-IR spectroscopy of calcium phosphate inorganic core coated with lactose having coating concentrations of a) 0.03 M, b) 0.06 M, and c) 0.09 M shows characteristic bonds for calcium phosphate inorganic core coated with lactose (FIGS. 5, 6 and 7, respectively). The characteristic bands observed for calcium phosphate inorganic core coated with lactose are given in table 2.

TABLE 2

Characteristic bands for calcium phosphate inorganic core coated with lactose

| | Observed in this study, cm$^{-1}$ | | |
|---|---|---|---|
| Characteristic bands | a) Coated core 0.03M | b) Coated core 0.06M | c) Coated core 0.09M |
| OH stretch | 2898.13 | 2895.28 | 2897.66 |
| CH₂ stretch | 3528.40 | 3665.35 | 2931.70 |
| OH bending | 3338.64 | 3044.92 | 3398.21 |
| C—O stretch | 1068.19 | 986.17 | 1428.00 |

Figure 8:
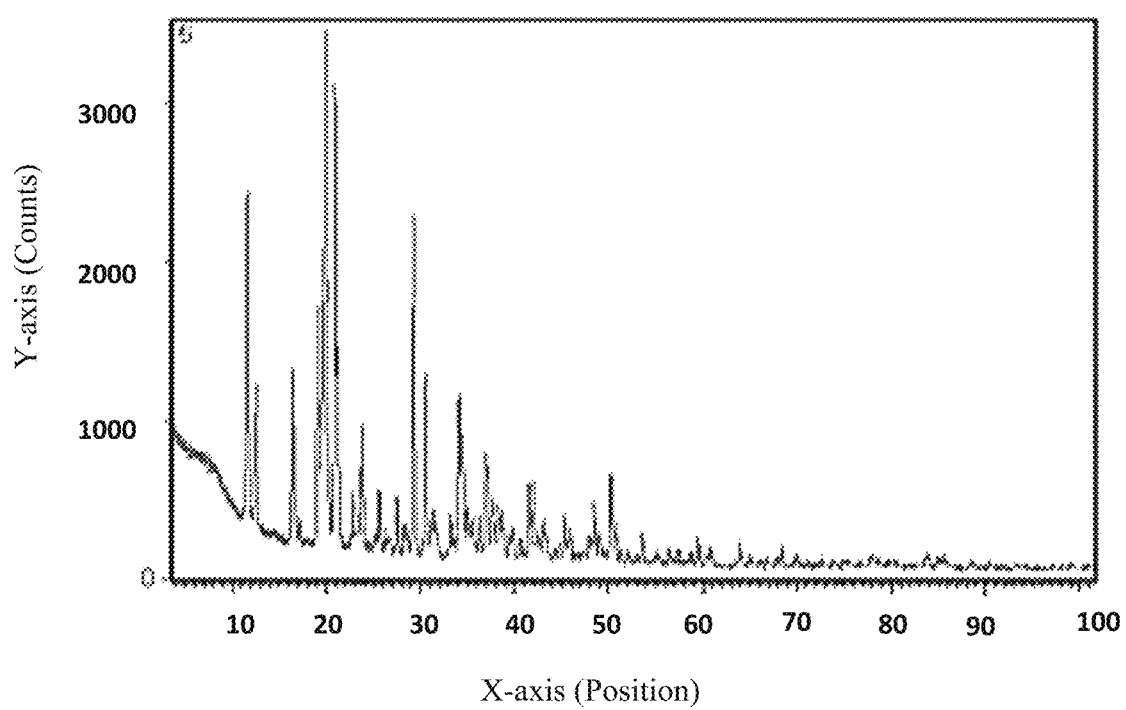
FIGS. 8-10 depict a X-ray diffractograms of the calcium phosphate inorganic core coated with lactose having coating concentrations of (a) 0.03M, (b) 0.06M and (c) 0.09M, respectively, wherein 'X-axis' denotes Position [°2Theta] (Copper) and 'Y-axis' denotes counts.
Figure 9:
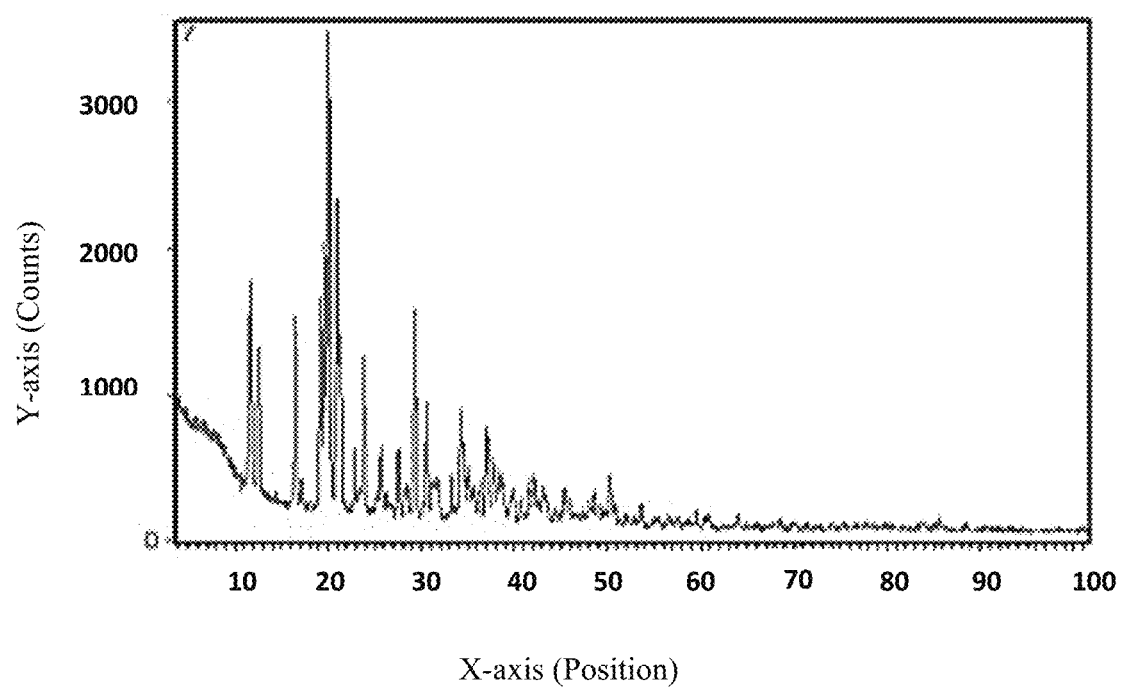
Figure 10:
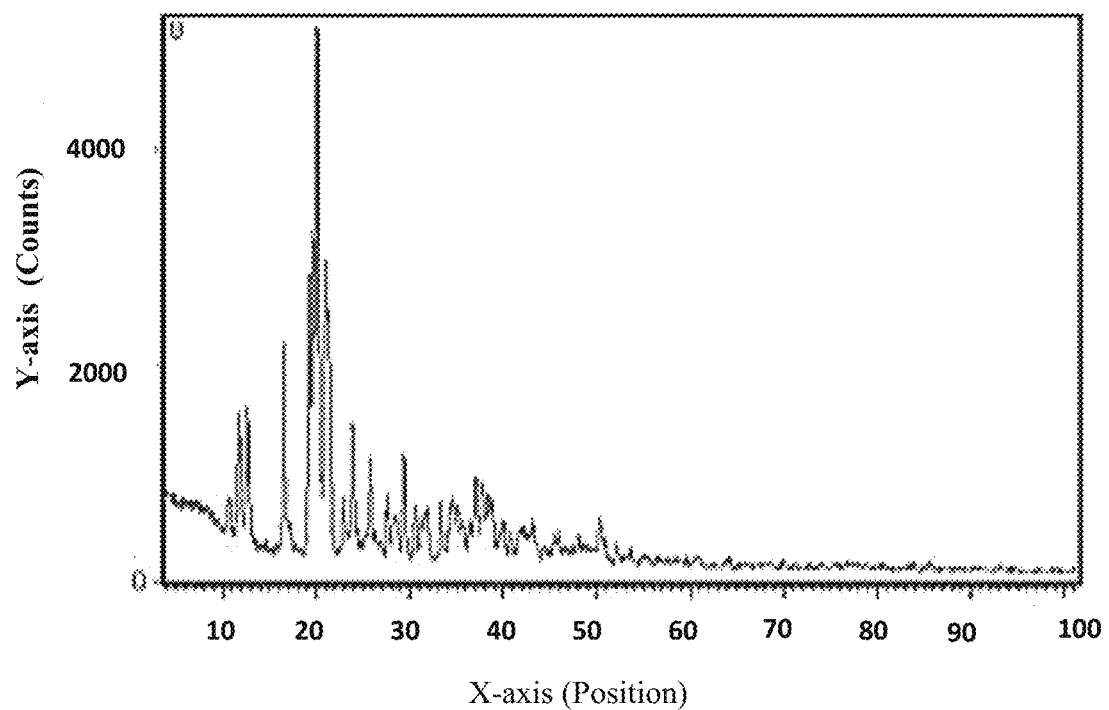

The X-ray diffractograms of the calcium phosphate inorganic core coated with lactose having coating concentrations of (a) 0.03M, (b) 0.06M and (c) 0.09M shows amorphous pattern of XRD for calcium phosphate inorganic core coated with lactose (FIGS. 8, 9 and 10, respectively).

Figure 11:
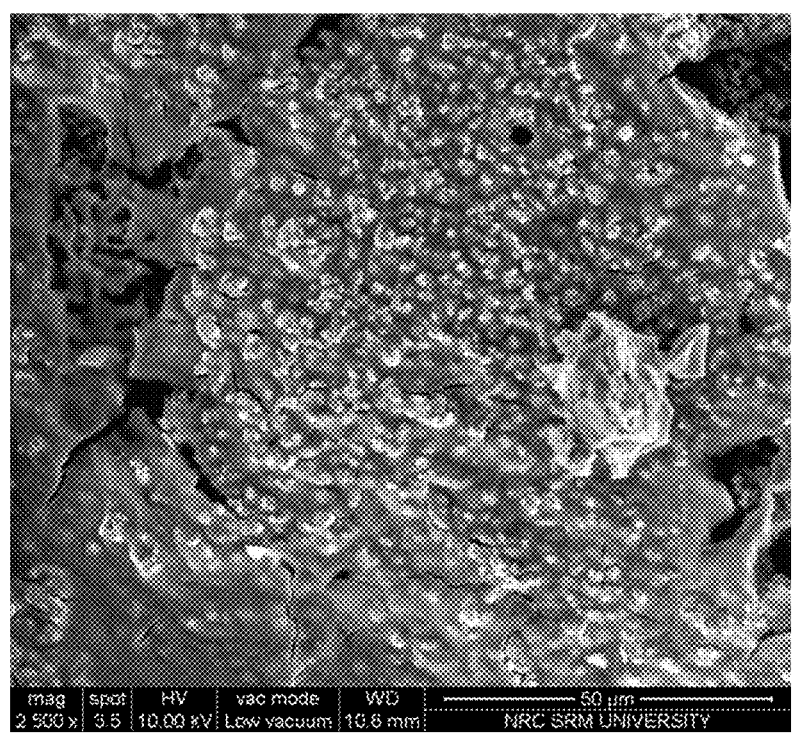
FIG. 11 depicts a Scanning electron microscopy of the lactose coated calcium phosphate core.

For morphological characterization, scanning electron microscopy (SEM) was used. The lactose coated calcium phosphate core was found to be spherical. The spherical shapes of the submicron carriers are evident from their SEM images (FIG. 11).

From FIGS. 8 to 11, it is evident that the calcium phosphate inorganic core coated with lactose is amorphous and spherical.

C. Preparation of Cefprozil Monohydrate Loaded Aquasomes

Cefprozil monohydrate (12.5 mg) and the lactose coated calcium phosphate (25 mg) were mixed under stirring for 90 minutes to obtain a third mixture. The so obtained third mixture was settled at 4° C. for 600 minutes to facilitate adsorption of cefprozil monohydrate on the lactose coated calcium phosphate. The settled third mixture was lyophilized to obtain cefprozil monohydrate loaded aquasomes.

These cefprozil monohydrate loaded aquasomes were characterized by using FT-IR spectroscopy, Zeta sizer, X-ray powder diffractograms (XRD), and Scanning electron microscopy (SEM).

Figure 12:
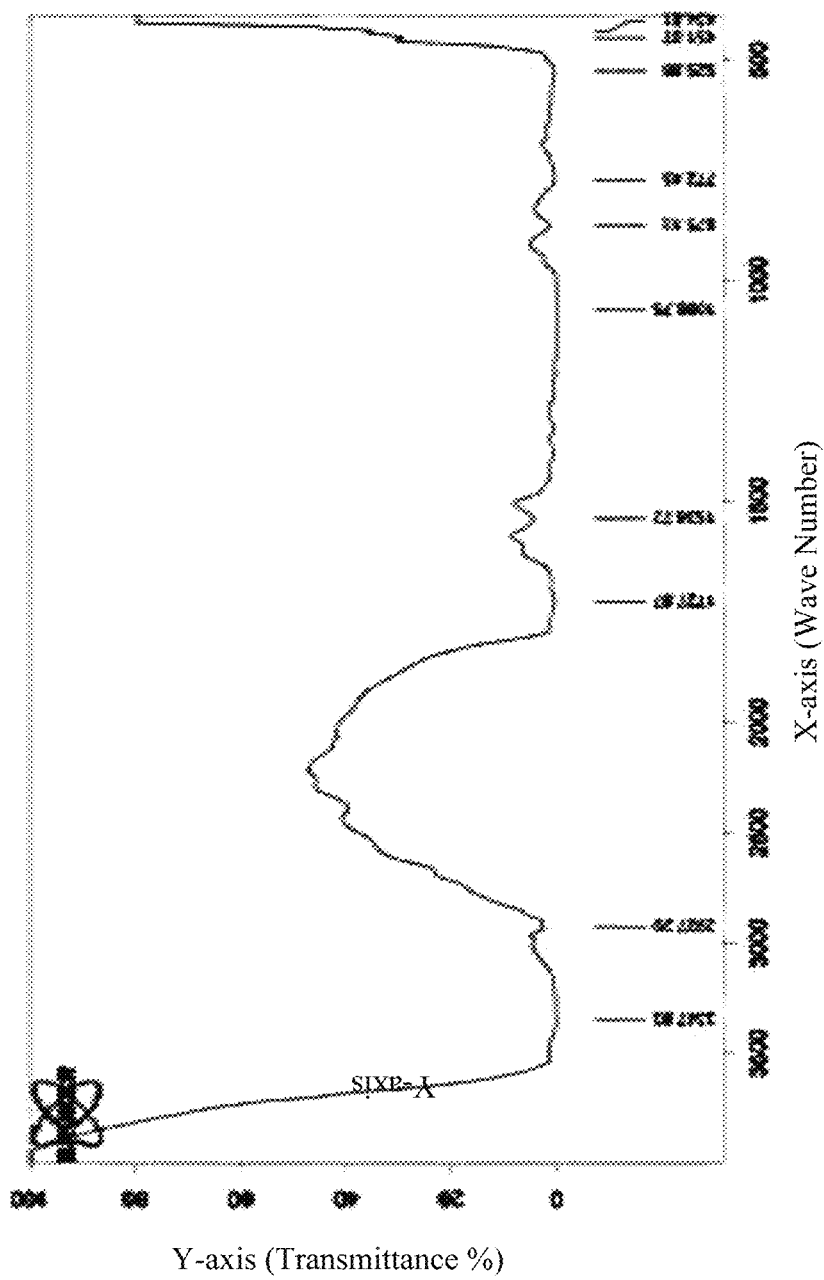
FIG. 12 depicts a FT-IR spectroscopy for Cefprozil monohydrate loaded aquasomes, wherein 'X-axis' denotes wavenumber and 'Y-axis' denotes Transmittance (%).

FT-IR spectrophotometer was used for confirming the formation of calcium phosphate core, presence of lactose on the calcium phosphate core, and the presence of drug (Cefprozil monohydrate) on lactose coated calcium phosphate core. The characteristic bands were observed and then interpreted (FIG. 12). The characteristic bands for cefprozil monohydrate are given in table 3.

TABLE 3

Characteristic bands for Cefprozil monohydrate loaded aquasomes

| Characteristic bands | Observed in this study, cm$^{-1}$ |
|---|---|
| N—H Stretch | 3347.93 |
| B-lactum ring | 1727.97 |
| C=O Stretch | 1538.72 |
| C—O Stretch | 1066.76 |
| C—H Stretch | 2927.20 |
| P—O Stretch | 875.13 |

FT-IR confirms the formation of cefprozil monohydrate loaded aquasomes.

The drug loading efficiency of cefprozil monohydrate on aquasomes was found to be 82.19%.

Figure 13:
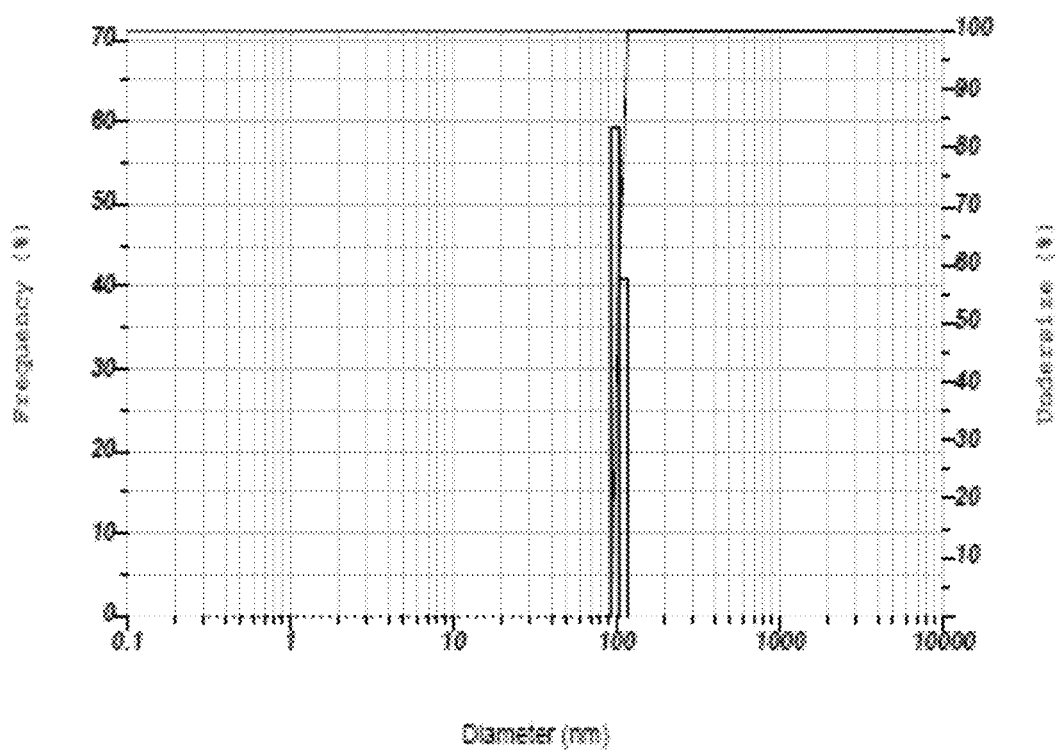
FIGS. 13 and 14 depict a graphical representation of particle size and zeta potential of cefprozil monohydrate loaded aquasomes.
Figure 14:
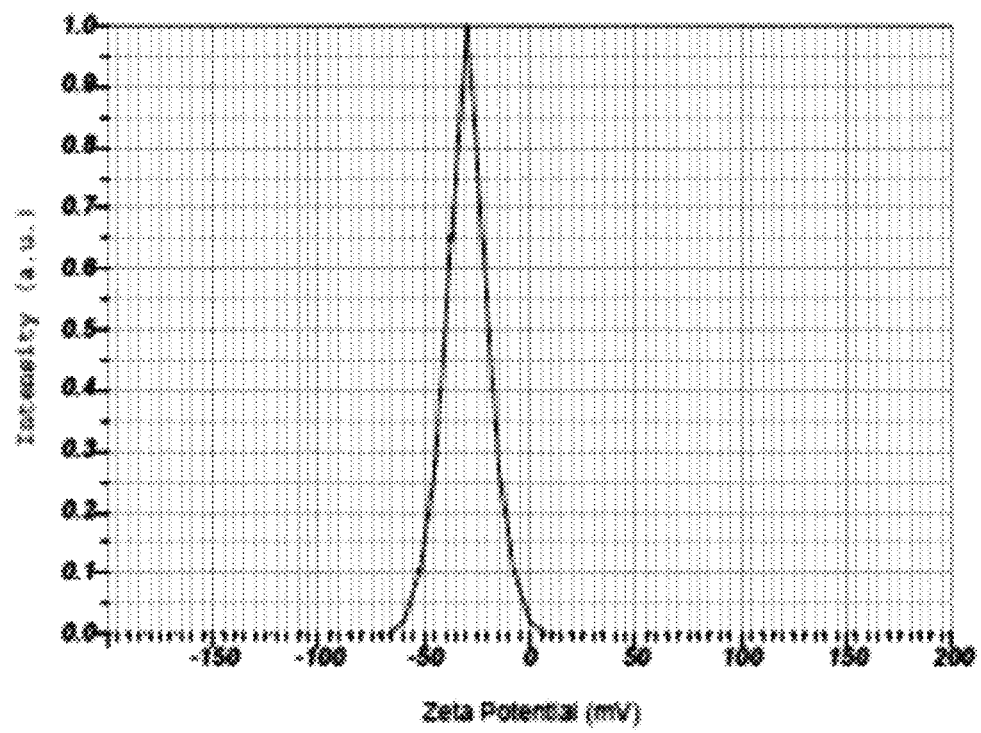

Zeta sizer shows the mean particle size and surface charge of cefprozil monohydrate loaded aquasomes, which determines particle stability in dispersion. The particle size of cefprozil monohydrate loaded aquasomes was given table 4. The mean particle size by zeta sizer for cefprozil monohydrate loaded aquasomes was found to be 104.1 nm and zeta potential is −29.8 mV (FIGS. 13 and 14). The mean particle size and zeta potential of cefprozil monohydrate loaded aquasomes confirms the stability of cefprozil monohydrate loaded aquasomes.

TABLE 4

Particle size of cefprozil monohydrate loaded aquasomes

| Peak No. | S.P. Area Ratio | Mean | SD | Mode |
|---|---|---|---|---|
| 1 | 1.00 | 104.1 nm | 6.3 nm | 103.1 nm |
| 2 | ___ | ___ nm | ___ nm | ___ nm |
| 3 | ___ | ___ nm | ___ nm | ___ nm |
| Total | 1.00 | 104.1 nm | 6.3 nm | 103.1 nm |

The zeta potential of cefprozil monohydrate loaded aquasomes is given in table 5.

TABLE 5

Zeta potential of cefprozil monohydrate loaded aquasomes

| Peak No | Zeta potential | Electrophoretic mobility |
|---|---|---|
| 1 | −29.8 mv | −0.000231 cm$^2$/Vs |
| 2 | ___ mv | ___ cm$^2$/Vs |
| 3 | ___ mv | ___ cm$^2$/Vs |

Figure 15:
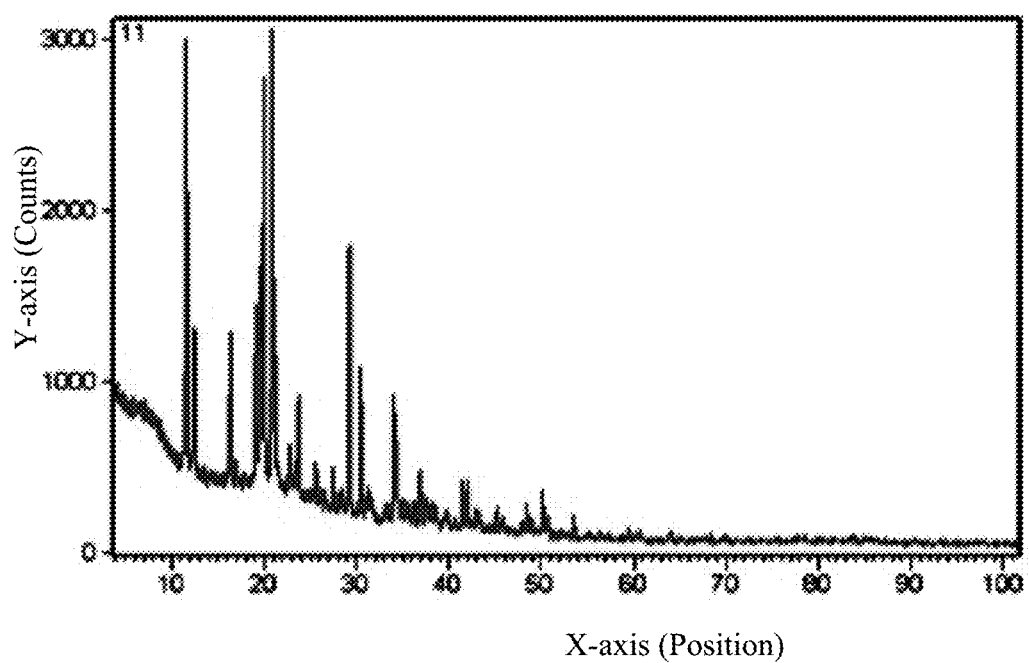
FIG. 15 depicts a X-ray powder diffractograms for cefprozil monohydrate loaded aquasomes, wherein 'X-axis' denotes Position [°2Theta](Copper) and 'Y-axis' denotes counts.

The X-ray diffractograms of the cefprozil monohydrate loaded aquasomes showed crystallinity behaviour after lactose coated calcium phosphate was loaded with cefprozil monohydrate, because cefprozil monohydrate was itself crystalline in nature (FIG. 15).

For morphological characterization, scanning electron microscopy (SEM) was used. The cefprozil monohydrate loaded aquasomes were found to be irregular and elongated in shape (FIG. 16).

Figure 16:
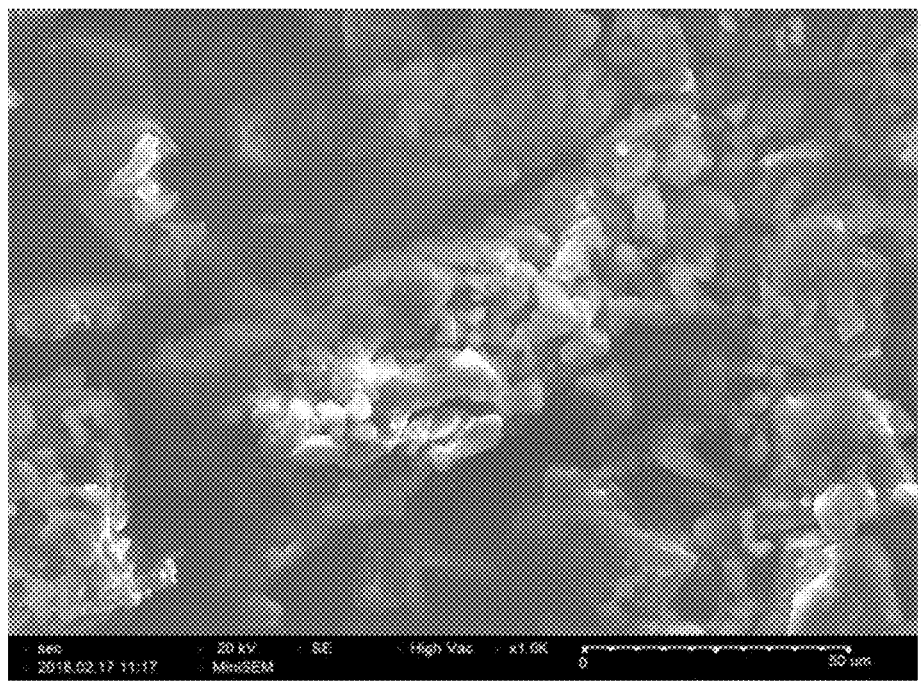
FIG. 16 depicts a Scanning electron microscopy of the cefprozil monohydrate loaded aquasomes.

From FIGS. 15 and 16, it is evident that the cefprozil monohydrate loaded aquasomes were crystalline in nature and hence highly soluble.

In Vitro Release Profile of Cefprozil Monohydrate Loaded Aquasome

Release study of cefprozil monohydrate from aquasomes was determined by Franz diffusion method. In this method, cellophane membrane was used as diffusion barrier, it was clamped between the donor and the receptor chamber of vertical diffusion cell type with an effective diffusion area of 2.8 cm$^2$ and a 7 ml cell volume. The receptor chamber was filled with freshly prepared buffer solution. The diffusion cell was maintained at 37° C. and the solution in the receptor chambers was stirred continuously at 50 rpm. The formulation (1 mg) was gently placed in the donor chamber. 2 ml sample was withdrawn with pipette at time interval of 15 minutes, 30 minutes, 45 minutes, 1 hour and later at every 1 hour intervals and replaced by the 2 ml of fresh 7.4 pH buffer.

These samples were filtered through 0.45 μm membrane filter and sodium hydroxide (1N) (1 ml) was added to each tube before heating at 100° C. for 15 minutes. After cooling, the volumes were transferred quantitatively into 10 ml volumetric flasks and the volume was adjusted to 10 ml with distilled water, mixed well before reading using UV spectrophotometer at λ 486 nm for cefprozil monohydrate against the appropriate blank (1 ml of 1N NaOH diluted to 10 ml with distilled water). A graph was constructed by plotting the absorbance values versus drug concentrations in μg/ml for the release profile of cefprozil monohydrate from aquasomes as provided in table 6.

TABLE 6

Release profile of cefprozil monohydrate from aquasomes

| Time hrs | Percentage cumulative drug release of cefprozil monohydrate loaded aquasomes |
|---|---|
| 0 | 0 |
| 0.25 | 13.71 |
| 0.5 | 19.67 |
| 0.75 | 34.81 |
| 1 | 48.59 |
| 2 | 56.79 |
| 3 | 67.65 |
| 4 | 71.32 |
| 5 | 77.21 |
| 6 | 81.59 |
| 7 | 83.45 |
| 8 | 84.52 |

It is evident from table 6 that the cefprozil monohydrate is released in controlled manner over a period of time.

Experiment 2: Composition of Gel Formulation (Antibiotic Loaded Aquasome-Nanocarrier Gel) in Accordance with the Present Disclosure Composition of gel formulation of the present disclosure was prepared using the following ingredients as given in Table-7.

TABLE 7

Ingredients of gel formulation

| Ingredients used | Composition 1 (wt %) | Composition 2 (wt %) |
|---|---|---|
| Cefprozil monohydrate loaded aquasomes | 19.41 | — |
| Cefuroxime axetil loaded aquasomes | — | 19.41 |
| 2-propenoic acid homopolymer (Carbopol 934 ™) | 77.66 | 77.66 |
| Methyl paraben | 0.15 | 0.15 |
| Propyl paraben | 0.05 | 0.05 |
| Water | 2.74 | 2.74 |

General Procedure for Preparing Gel Formulation:

The predetermined amount of 2-propenoic acid homopolymer (sold under the trademark Carbopol 934), water and a preservative were mixed to obtain a gel base. To the so obtained gel base, antibiotic loaded aquasome-nanocarrier (Cefprozil monohydrate loaded aquasome-nanocarrier and Cefuroxime axetil loaded aquasome-nanocarrier) was added under continuous stirring to obtain a gel formulation (antibiotic loaded aquasome-nanocarrier gel).

The gel formulation was characterized for their physicochemical properties which are given below in table 8.

TABLE 8

Physicochemical properties of gel formulation

| Sr. No. | Parameter | Results |
| --- | --- | --- |
| 1. | Appearance | White |
| 2. | Homogeneity | Good |
| 3. | pH | 6.9 |
| 4. | Spreading capacity | 2615 |
| 5. | Viscosity (cp) | 3264 |

Microbiological Study:

The cefprozil monohydrate loaded calcium phosphate core and gel formulation (cefprozil monohydrate loaded aquasome-nanocarriers gel) were studied for antibacterial activity against Staphylococcus aureus and Klebseilla. The zone of inhibition for Staphylococcus aureus using cefprozil monohydrate loaded calcium phosphate core and gel formulation (cefprozil monohydrate loaded aquasome-nanocarriers gel) were found to be 13.0±0.2 mm, and 10±0.1 mm, respectively. The zone of inhibition for Klebseilla using cefprozil monohydrate loaded calcium phosphate core and gel formulation (cefprozil monohydrate loaded aquasome-nanocarriers gel) were found to be 14±0.1 mm, and 31±0.2 mm, respectively (FIG. 17).

Figure 17:
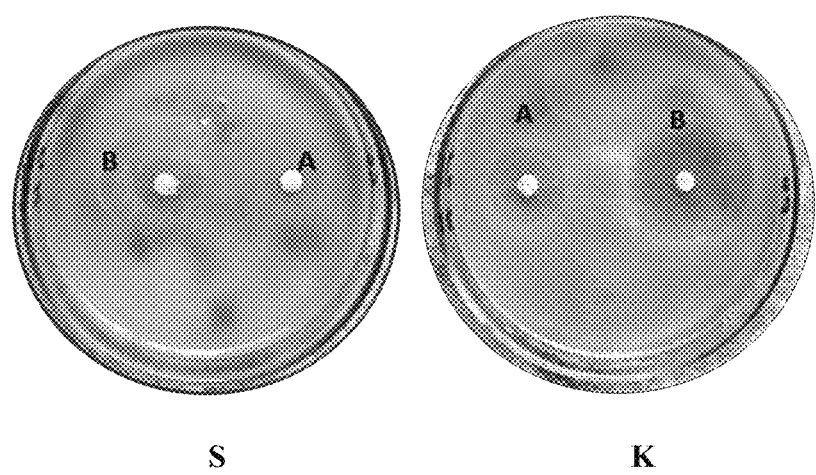
FIG. 17 depicts zone of inhibitions of cefprozil monohydrate loaded aquasomes (denoted as 'A') and gel formulation [cefprozil monohydrate loaded aquasome-nanocarriers gel] (denoted as 'B') against *Staphylococcus aureus* (denoted by 'S') and *Klebseilla* (denoted by 'K').

From FIG. 17, it is evident that the gel formulation (cefprozil monohydrate loaded aquasome-nanocarriers gel) has good antibacterial activity against bacteria such as Staphylococcus aureus and Klebseilla.

Stability Study:

The stability of the gel formulation was assessed according to ICH guidelines. The gel formulation was kept for 6 months in humidity chamber maintained at 30±2° C./65±5% RH and 40±2° C./75±5% RH.

After stability studies, the gel formulation was characterized for their physicochemical properties which are given below in table 9.

TABLE 9

Physicochemical properties of gel formulation

| Sr. No. | Parameter | Results |
| --- | --- | --- |
| 1. | Appearance | White |
| 2. | Homogeneity | Good |
| 3. | pH | 6.9 |
| 4. | Spreading capacity | 2615 |
| 5. | Viscosity (cp) | 3264 |
| 6. | Drug content | 98.83% |
| 7. | Flow behaviour | Shear thinning |

From table 8 and 9, it can be concluded that at the end of 6 months, the prepared formulation (cefprozil monohydrate loaded aquasome-nanocarriers gel) is found to be stable at 30±2° C. at 65±5 RH, as no significant changes in the parameters of the gel formulation were observed.

Comparative In Vitro Drug Release Study of the Gel Formulation (Cefprozil Monohydrate Loaded Aquasome-Nanocarriers Gel) Before and after Stability Study In vitro drug release study of cefprozil monohydrate from gel formulation before and after stability study was determined by Franz diffusion method. In this method, cellophane membrane was used as diffusion barrier, it was clamped between the donor and the receptor chamber of vertical diffusion cell type with an effective diffusion area of 2.8 cm$^2$ and a 7 ml cell volume. The receptor chamber was filled with freshly prepared buffer solution. The diffusion cell was maintained at 37° C. and the solution in the receptor chambers was stirred continuously at 50 rpm. The formulation (1 mg) was gently placed in the donor chamber. 2 ml sample was withdrawn with pipette at time interval of 15 minutes, 30 minutes, 45 minutes, 1 hour and later at every 1 hour intervals and replaced by the 2 ml of fresh 7.4 pH buffer.

These samples were filtered through 0.45 μm membrane filter and sodium hydroxide (1N) (1 ml) was added to each tube before heating at 100° C. for 15 minutes. After cooling, the volumes were transferred quantitatively into 10 ml volumetric flasks and the volume was adjusted to 10 ml with distilled water, mixed well before reading using UV spectrophotometer at A 486 nm for cefprozil monohydrate. The release profile of cefprozil monohydrate from aquasomes is shown in FIG. 18.

Figure 18:
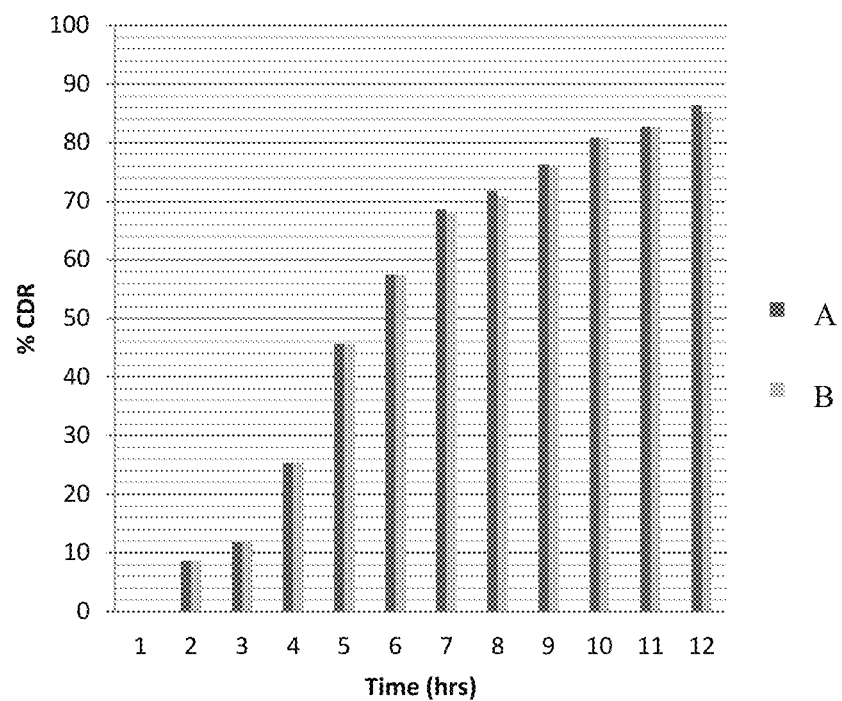
FIG. 18 depicts a graphical representation comparing in vitro drug release profile between gel formulation of the present disclosure before (denoted as 'A') and after stability study (denoted as 'B').

It is evident from FIG. 18 that the in vitro release of cefprozil monohydrate from gel formulation before and after stability study is similar, which means the gel formulation of the present disclosure is stable over a period of 6 months.

Figure 19:
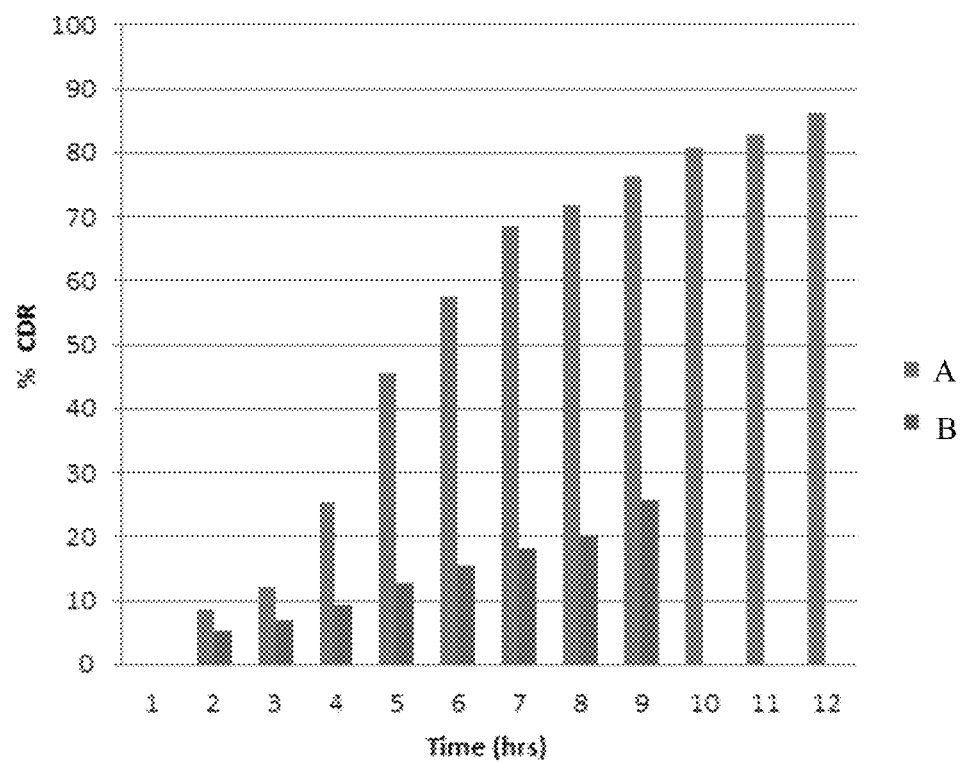
FIG. 19 depicts a graphical representation comparing in vitro drug release profile between conventional gel (denoted as 'A') and gel formulation of the present disclosure (denoted as 'B').

Comparative In Vitro Drug Release Study of Conventional Gel and the Gel Formulation (Cefprozil Monohydrate Loaded Aquasome-Nanocarriers Gel) of the Present Disclosure The in vitro drug release study was carried out by the process mentioned hereinabove. The release profile of drug from conventional gel and from gel formulation of the present disclosure is shown in FIG. 19. The conventional gel formula is given in table 10.

TABLE 10

Conventional gel formula

| S. No. | Ingredients | Quantity |
| --- | --- | --- |
| 1 | Cefprozil monohydrate (fine powder) | 0.005 g |
| 2 | Carbopol 934 ™ | 1 g |
| 3 | Methyl paraben | 0.15% w/v |
| 4 | Propyl paraben | 0.05% w/v |
| 5 | Water | 15 ml |

It is evident from FIG. 19 that the release was very less in conventional gel as compared to the gel formulation of the present disclosure as the nano scale of the drug loaded formulation of the present disclosure showed more promising permeation viz a viz absorption due to enhanced solubility characteristics. This paved the way for increased drug release at the studied pH of the wound infection.

Animal Study:

The animal study was conducted after due permission from institutional animal ethical committee with the approval number IAEC 168/2015, on diabetes induced albino wistar rats, diabetes foot wound was treated with the gel formulation having cefprozil monohydrate loaded aquasomes, the tested animals showed promising wound healing effect during the study period.

Overall, from the above results, it is evident that the gel formulation has improved stability, and solubility. Also, the gel formulation has enhanced bioavailability and therapeutic efficacy while treating diabetic foot ulcer infections.

Technical Advancements

The present disclosure described herein above has several technical advantages including, but not limited to, the realization of a gel formulation that:

is stable;

has improved solubility;

has enhanced bioavailability; and has enhanced therapeutic efficacy while treating diabetic foot ulcer infections.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

I claim:

1. A gel formulation for treating diabetic foot ulcer infections, said formulation comprising:
   antibiotic loaded aquasomes having a diameter in the range of 80 nm to 120 nm as measured by a zeta sizer instrument;
   a gelling agent;
   a preservative; and
   a fluid medium,
   wherein said antibiotic loaded aquasomes includes antibiotic loaded on a polyhydroxy oligomer coated calcium phosphate,
   wherein said polyhydroxy oligomer is selected from the group consisting of lactose, trehalose, and cellobiose,
   wherein said antibiotic loaded aquasomes include a calcium phosphate core having a particle diameter in the range of 45 nm to 55 nm as measured by a zeta sizer instrument, coated with polyhydroxy oligomer thereon followed by coating of an antibiotic on said aquasomes,
   wherein said aquasomes are in an amount in the range of 15 wt % to 20 wt % of the total weight of said formulation; said gelling agent is in an amount in the range of 70 wt % to 90 wt % of the total weight of said formulation; said preservative is in an amount in the range of 0.05 wt % to 0.25 wt % of the total weight of said formulation; and said fluid medium is in an amount in the range of 1 wt % to 4 wt % of the total weight of said formulation,
   wherein the pH of said gel formulation is in the range of 6.0 to 7.0, and
   wherein the said the gel formulation is stable over the period of 6 months.

2. The formulation as claimed in claim 1, wherein said aquasomes are in an amount of 19.4 wt % of the total weight of said formulation; said gelling agent is in an amount of 77.66 wt % of the total weight of said formulation; said preservative is in an amount of 0.2 wt % of the total weight of said formulation; and said fluid medium is in an amount of 2.74 wt % of the total weight of said formulation.

3. The formulation as claimed in claim 1, wherein said antibiotic is cephalosporin.

4. The formulation as claimed in claim 1, wherein said antibiotic is selected from cefprozil monohydrate and cefuroxime axetil.

5. The formulation as claimed in claim 1, wherein said gelling agent is selected from the group consisting of 2-propenoic acid homopolymer, acacia, pectin, methyl cellulose, ethyl cellulose, hydroxyl propyl methyl cellulose, and sodium alginate.

6. The formulation as claimed in claim 1, wherein said preservative is at least one selected from the group consisting of methyl paraben, propyl paraben, benzoic acid, sodium benzoate, and cholocresol.

7. The formulation as claimed in claim 1, wherein said fluid medium is selected from the group consisting of water, ethanol, benzene, acetone, and phosphate buffer.

8. A process for preparing a gel formulation as claimed in claim 1, said process comprising the following steps:
   I. preparing antibiotic loaded aquasomes using following steps:
      a. reacting disodium hydrogen phosphate solution and calcium chloride solution under continuous stirring to obtain a first mixture comprising precipitated calcium phosphate;
      b. separating said precipitated calcium phosphate from said first mixture and washing said precipitated calcium phosphate with water to obtain calcium phosphate;
      c. suspending said calcium phosphate in water and filtering to obtain filtered calcium phosphate;

d. lyophilizing said filtered calcium phosphate to obtain a core of calcium phosphate;
e. admixing said core of calcium phosphate and a polyhydroxy oligomer to obtain a second mixture, followed by sonicating said second mixture for a time period in the range of 10 minutes to 20 minutes to obtain a suspension and settling said suspension at a temperature in the range of 2° C. to 8° C. for a time period in the range of 360 minutes to 600 minutes;
f. lyophilizing said settled suspension to obtain a polyhydroxy oligomer coated calcium phosphate;
g. mixing antibiotic and said polyhydroxy oligomer coated calcium phosphate under stirring for a time period in the range of 80 minutes to 100 minutes to obtain a third mixture and settling said third mixture at a temperature in the range of 2° C. to 8° C. for a time period in the range of 360 minutes to 600 minutes; and
h. lyophilizing said settled third mixture to obtain antibiotic loaded aquasomes; and
II. blending said aquasomes of step (I) with a gelling agent, a preservative, and a fluid medium to obtain a gel formulation.

9. The process as claimed in claim 8, wherein the molar ratio of said disodium hydrogen phosphate solution to said calcium chloride solution is 1:1.

10. The process as claimed in claim 8, wherein said filtration of step (c) is carried out using 0.22 μm Millipore filter.

11. The process as claimed in claim 8, wherein particle diameter of said core of calcium phosphate is in the range of 45 nm to 55 nm.

12. The process as claimed in claim 8, wherein said polyhydroxy oligomer is selected from the group consisting of lactose, trehalose, and cellobiose.

13. The process as claimed in claim 8, wherein the weight ratio of said polyhydroxy oligomer to said core of calcium phosphate is 1:2.

14. The process as claimed in claim 8, wherein the weight ratio of said antibiotic to said polyhydroxy oligomer coated calcium phosphate is 1:2.

15. A method for treatment of diabetic foot ulcer infections in mammals, the method comprising topical application of an effective amount of the gel formulation as claimed in claim 1 to the diabetic foot ulcer.

16. The method as claimed in claim 15, wherein said effective amount of said gel formulation is in the range of 2 mg to 20 mg.

* * * * *